(12) United States Patent
Lerner

(10) Patent No.: US 6,399,649 B1
(45) Date of Patent: Jun. 4, 2002

(54) COMPOSITIONS AND METHODS FOR THE TREATMENT OF CHRONIC LYMPHOCYTIC LEUKEMIA

(75) Inventor: Adam Lerner, Newton Highlands, MA (US)

(73) Assignee: Boston Medical Center Corporation, Boston, MA (US)

( * ) Notice: Subject to any disclaimer, the term of this patent is extended or adjusted under 35 U.S.C. 154(b) by 0 days.

(21) Appl. No.: 09/423,349

(22) PCT Filed: Sep. 17, 1999

(86) PCT No.: PCT/US99/21518

§ 371 (c)(1),
(2), (4) Date: May 1, 2000

(87) PCT Pub. No.: WO00/16621

PCT Pub. Date: Mar. 30, 2000

Related U.S. Application Data
(60) Provisional application No. 60/101,721, filed on Sep. 24, 1998.

(51) Int. Cl.[7] .............................................. A61K 31/40
(52) U.S. Cl. ..................................................... 514/423
(58) Field of Search ......................................... 514/423

(56) References Cited

U.S. PATENT DOCUMENTS

| | | | |
|---|---|---|---|
| 5,529,914 A | 6/1996 | Hubbell et al. | 435/182 |
| 5,573,934 A | 11/1996 | Hubbell et al. | 435/177 |
| 5,591,776 A | 1/1997 | Cavalla et al. | 514/662 |
| 5,601,844 A | 2/1997 | Kagayama et al. | 44/489 |
| 5,622,977 A | 4/1997 | Warrellow et al. | 514/336 |

OTHER PUBLICATIONS

Devita, V.T., Rosenberg, S.A., Hellman, S., "Cancer: Principles & Practice of Oncology." 3rd. ed., J. B. Lippincott Company, pp. 1843–1847 (1989).

Daniel, V. et al., "Induction of cytolysis of cultured lymphoma cells by adenosine 3':5'–cyclic monophosphate and isolation of resistant variants." Proc. Natl. Acad. Sci. USA, 70:76 (1973).

Lomo, J. et al., "TGB–b1 and cyclic AMP promote apoptosis in resting human B lymphocytes." J. Immunol., 154:1634 (1954).

Schwabe, U. et al., "4–(3–cyclopentyloxy–4methoxyphenyl)–2pyrrilidone (ZK 62711): a potent inhibitor of adenosine cyclic 3',5'–monophosphate phosphodiesterases in homogenates and tissue slices from rat brain." Molecular Pharmacology, 12:900 (1976).

Sheppard, H. et al., "Structure–activity relationships for inhibitors of phosphodiesterase from erythrocytes and other tissues." Adv. Cyclic Nucl. Res., 1:103 (1972).

Silber, R and Stahl, R., "Chronic lymphocytic leukemia and related diseases." In Hematology 4th ed., W.J. Williams et al. Eds., McGraw–Hill, Inc., pp. 1005–1025 (1990).

Brown, B.A., "Hematology: Principles and Procedures." 3th ed. Lea & Febiger, PA, pp. 248–250 (1980).

Dale, D. C. and Federman, D.D. "The leukemias and the myeloproliferative disorders." Scientific American Medicine 2:16–29 (1996).

Mentz, F. et al. "Theophylline a new inducer of apoptosis in B–CLL: role of cyclic nucleotides." British Journal of Haematology 90:957–959 (1995).

Mentz, F. et al. "Theophylline synergizes with chlorambucil in inducing apoptosis of B–chronic lymphocytic leukemia cells." Blood 88:2172–2182 (1996).

Zurbonsen K. et al. "Dissociation between phosphodiesterase inhibition and antiproliferative effects of phosphodiesterase inhibitors on the dami cell line." Biochemical Pharmacology 53:1141–1147 (1997).

Weiss, B. and Hait, W.N. "Selective cyclic nucleotide phosphodiesterase inhibitors as potential therapeutic agents." Ann. Rev. Pharmacol. Toxicol. 17:441–477 (1977).

Drees, M. et al. "3',5'–cyclic nucleotide phosphodiesterase in tumor cells as potential target dor tumor growth inhibition." Cancer Research 53:3058–3061 (1993).

Zhu W–H. et al. "Cyclic AMP–specific phosphodiesterase inhibitor rolipam and RO–20–1724 promoted apoptosis in HL60 promyelocytic leukemic cells via cyclic AMP–independent mechanism." Life Sci. 63:265–74 (1998).

Zhu et al., Life Sci., 63(4), 265–274 Abstract Only, 1998.*
Kim et al., Blood, 92(7), 2484–2494 Abstract Only, 1998.*

* cited by examiner

Primary Examiner—Jerome D. Goldberg
(74) Attorney, Agent, or Firm—Nixon Peabody LLP

(57) ABSTRACT

Methods for treating patients with CLL with pharmaceutical agents are disclosed. The methods of the present invention can be used in patients that have not responded to standard treatment. In addition, the methods can be used to augment the impact of standard chemotherapy.

7 Claims, 14 Drawing Sheets

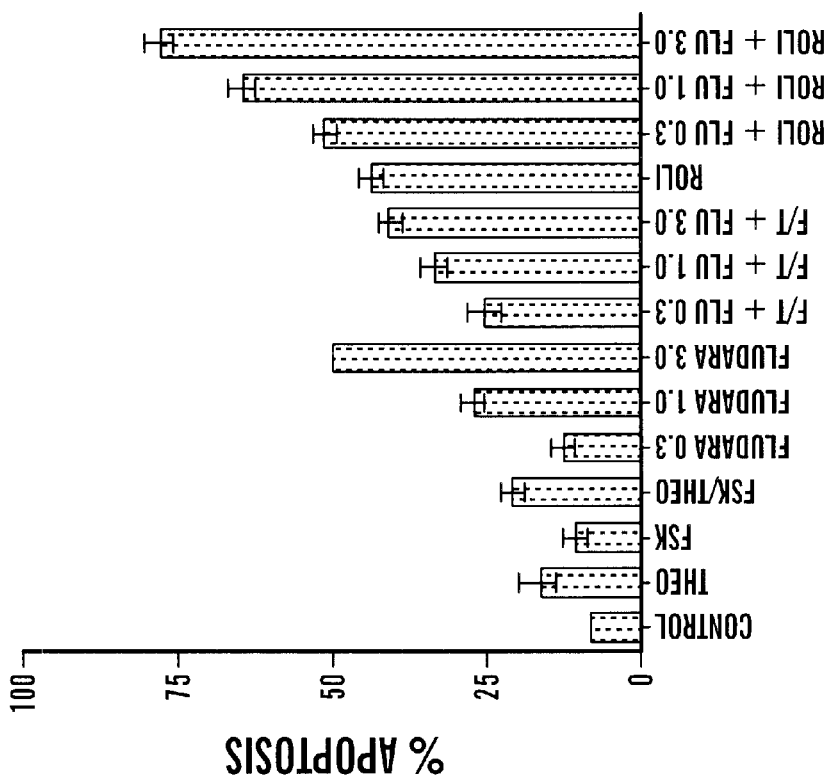
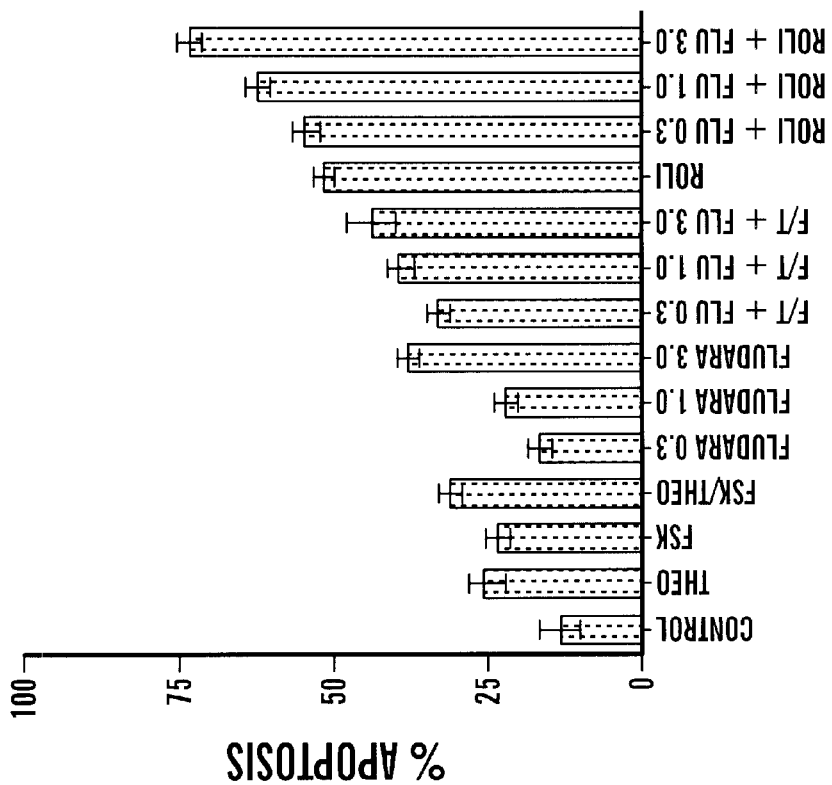
FIG. 12A
FIG. 12B

COMPOSITIONS AND METHODS FOR THE TREATMENT OF CHRONIC LYMPHOCYTIC LEUKEMIA

This application is a 371 of PCT/US99/21518 filed Sep. 17, 1999 which claims benefit of Ser. No. 60/101,721 filed Sep. 24, 1998

FIELD OF THE INVENTION

The present invention pertains to the treatment of patients with chronic lymphocytic leukemia (CLL) with pharmaceutical compositions comprising Type 4 cyclic adenosine monophosphate phosphodiesterase inhibitors, and more particularly, with an inhibitor that specifically inhibits Type 4 cyclic adenosine monophosphate phosphodiesterase.

BACKGROUND

Leukemias are malignant neoplasms of hematopoietic tissues. These neoplasms are categorized into two predominant forms: chronic and acute. While acute leukemias are characterized by undifferentiated cell populations, chronic leukemias usually present a more mature morphology. Notwithstandmg these classifications, however, the pathological impairment of normal hematopoiesis is the hallmark of all leukemias.

Chronic lymphocytic leukemia (CLL) is a neoplasm in which a clonal expansion of small lymphocytes accumulate in the marrow, lymph nodes, blood, spleen liver, and sometime other organs. The CLL cell is the neoplastic counterpart of an immunologically immature, incompetent lymphocyte. In over 95 percent of the cases, the clonal expansion is of a B-cell lineage. *See Cancer: Principles & Practice of Oncology* (3rd Edition) (1989) (pp. 1843–1847). In less than 5 percent of cases the tumor cells have a T-cell phenotype.

CLL, while accounting for only about 0.8 percent of all cancers in the United States, is the most prevalent leukemia afflicting adults in modern. countries, accounting for 30 percent of all leukemias. A majority of patients are over 60 years at the time of disease and 90 percent are over age 50.

Most patients are diagnosed following a routine physical examination or a blood count. The earliest and most frequent symptoms are fatigue and malaise. Later symptoms include lymphadenopathy and splenomegaly. Anemia and thrombocytopenia is found in approximately 15 percent of patients.

The general goal of leukemia therapy is to arrest the proliferation of abnormal morphologies and restore "normal" hematopoiesis in the bone marrow. Treatment regimens include chemotherapy. Unfortunately, chemotherapy is not always successful. Indeed, while CLL patients may have initial clinical responses to alkylating agents such as chlorambucil or adenosine analogs such as fludarabine, many ultimately become refractory to therapy. Consequently, there is a pressing need for the identification of novel approaches to this disease.

SUMMARY OF THE INVENTION

The present invention pertains to the treatment of patients with chronic lymphocytic leukemia with pharmaceutical compositions comprising Type 4 cyclic adenosine monophosphate phosphodiesterase inhibitors, and more particularly, with an inhibitor that specifically inhibits Type 4 cyclic adenosine monophosphate phosphodiesterase. One embodiment of the present invention contemplates a method comprising: a) providing: i) a patient having symptoms of chronic lymphocytic leukemia, and ii) a formulation comprising an inhibitor that specifically inhibits Type 4 cyclic adenosine monophosphate phosphodiesterases; and b) administration of a therapeutically effective dose of said formulation to said patient under conditions such that said symptoms are reduced.

The present invention is not limited by the method of administration. In one embodiment, the administration is enteral administration. In another embodiment, said enteral administration is oral administration. In still another embodiment, said administration is parenteral administration. In these embodiments, said parenteral administration can be topical administration or by a transdermal patch. In another embodiment, said parenteral administration is subcutaneous administration. While in still another embodiment, said parenteral administration utilizes an aerosol.

The present invention is not limited by the nature of the patient. In one embodiment, said patient is a naive patient (e.g., has not undergone prior treatment for CLL), while in other embodiments said patient is unresponsive or refractory to standard chemotherapy (e.g., alkylating agents). In still another embodiment, said patient is immunocompromised. In one embodiment, said patient is over fifty years of age.

The present invention is also not limited by the method of determining response to treatment. In one embodiment, said symptoms comprise lymphadenopathy and splenomegaly. In a yet another embodiment, said symptoms comprise the histology of a lymph node that is consistent with CLL.

The present invention contemplates usage of a variety of specific inhibitors. A preferred inhibitor is rolipram. While it is not intended that the present invention be limited to a specific mechanism by which the inhibitors of the present invention achieve therapeutic success, it has been empirically found (as the data herein shows) that the specific inhibitors of the present invention (e.g., rolipram) augment apoptosis induced by commonly used drugs (e.g., doxorubicin, chlorambucil and fludarabine). Consequently, the present invention specifically contemplates the use of the inhibitors in combination with other drugs, including but not limited to cytotoxic drugs.

Definitions

As used herein, the term "enteral administration" means the introduction of a composition to a patient such that it is absorbed in the intestinal tract of the patient (e.g., pill, tablet, elixir, etc.)

As used herein, the term "oral administration" means the introduction of a composition to a patient through the oral cavity (i.e., in the mouth).

As used herein, the term "parenteral administration" means administration of a composition other than enteral (e.g., injection, transdermal, aerosol, etc.).

As used herein, the term "topical administration" means the introduction of a composition to a patient by application to the surface of the skin.

As used herein, the term, "subcutaneous administration" means introduction of a composition to a patient under the surface of the skin (e.g., injection with a hypodermic needle).

As used herein, the phrase "naive patient" refers to a patient that has not undergone prior treatment for chronic lymphocytic leukemia.

As used herein, the phrase "an inhibitor that specifically inhibits Type 4 cyclic adenosine monophosphate phosphodiesterase" refers to a compound that inhibits Type 4 but not Type 1 or 3 phosphodiesterases. Of course, background level inhibition of Type 1 or 3 phosphodiesterases is permitted within the definition. Where the inhibitor inhibits Type 4 as well as Type 1 and/or 3, but inhibits Type 4 to a greater extent (the amounts being subject to quantitative determination by assays described herein), the phrase "preferentially inhibits Type 4 phosphodiesterases" is used herein (as distinct from "Type 4 specific."

DESCRIPTION OF THE FIGURES

FIG. 12 graphically shows that rolipram augments fludarabine-induced apoptosis in CLL cells.

DESCRIPTION OF THE INVENTION

Figure 1:
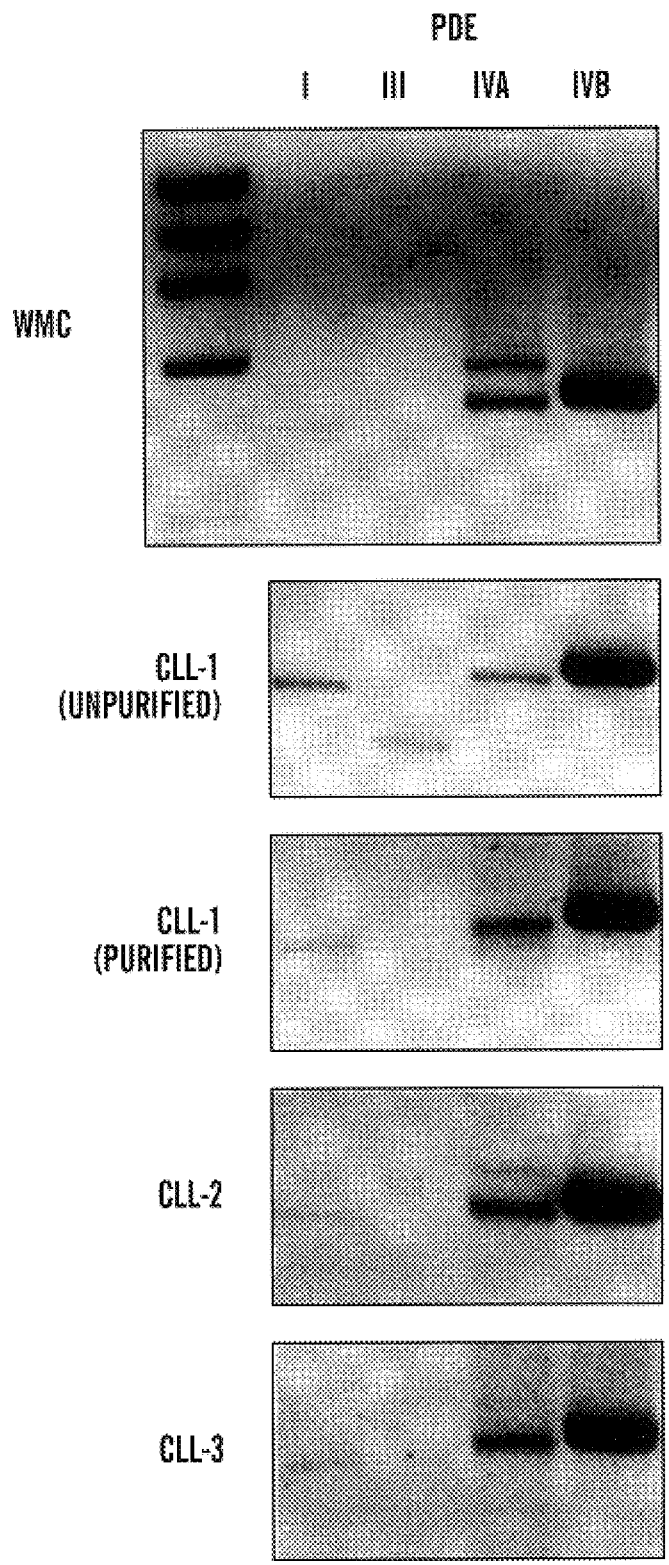
FIG. 1 is a gel showing the results of PCR on normal and CLL cells using oligonucleotides specific for human phosphodiesterases.

The present invention pertains to the treatment of patients with chronic lymphocytic leukemia with pharmaceutical compositions comprising Type 4 cyclic adenosine monophosphate phosphodiesterase inhibitors, and more particularly, with an inhibitor that specifically inhibits Type 4 cyclic adenosine monophosphate phosphodiesterase. The description of the invention discusses 1) apoptosis generally, 2) phosphodiesterases as a target for CLL therapy, and 3) treating CLL patients.

A. Apoptosis and Intracellular cAMP Levels

The first observation that some lymphoid cells die following exposure to agents that raise intracellular cAMP levels was made by Daniel et al. who found that the murine lymphoma cell line S49.1 underwent cytolysis following 48 hours of exposure to the combination of theophylline and a cell permeable 3':5' cyclic AMP analog, dibutyryl cAMP (dbcAMP). V. Daniel et al., "Induction of cytolysis of cultured lymphoma cells by adenosine 3':5'-cyclic monophosphate and isolation of resistant variants," *Proc. Natl. Acad. Sci. USA* 70:76 (1973). When mutant S49.1 clones resistant to the cytolytic effects of dbcAMP were isolated in soft agar, they were shown to be defective in the regulatory subunit of protein kinase A, confirming that cytolysis occurred as a direct result of PKA-mediated phosphorylation of unknown lymphoid target proteins. Subsequent work has demonstrated that cAMP-induced cytolysis occurs by apoptosis. D. J. McConkey et al., "Agents that elevate cAMP stimulate DNA fragmentation in thymocytes," *J. Immunol.* 145:1227 (1990). Certain normal T and B lymphoid subsets express the same marked sensitivity to cAMP-induced toxicity as tumor cell lines. Within the T lineage, CD4+CD8+ thymocytes appear to be more sensitive to the induction of apoptosis by cAMP than mature T cells. Apoptosis in resting human B lymphocytes, which occurs spontaneously at a high rate in culture, can be augmented by the addition of stimuli which elevate intracellular cAMP levels, such as the diterpene adenylate cyclase activator forskolin. J. Lomo et al., "TGF-b1 and cyclic AMP promote apoptosis in resting human B lymphocytes," *J. Immunol.* 154:1634 (1995).

B. Phosphodiesterases as a Target for Therapy of CLL

Cyclic AMP is catabolized within cells to 5'-AMP by 3':5' cAMP phosphodiesterases (PDE), a diverse group of enzymes encompassing 15 gene products and 7 classes of enzymes which have proven to be the target of successful pharmaceutical agents for neurologic, cardiovascular and inflammatory disorders. Despite this large array of cyclic nucleotide PDEs, only a subset of these enzymes have been reported in human lymphoid cells. Among them, the most commonly reported enzymes in human T cells are types 1, 3 and 4. Calcium-calmodulin dependent type 1 PDE activity has been detected in phytohemagglutinin-stimulated but not resting peripheral blood lymphocytes. One isoform from this family, PDE1B1, was recently detected in acute lymphocytic leukemia cells; inhibition of this enzyme was reported to induce apoptosis. PDE1 enzymes, which can catalyze the degradation of both cAMP and cGMP, are specifically inhibited by vinpocetine (IC50=21 mMol/L). Two groups have reported both type 3 and type 4 PDE in human T lymphocytes; lectin-mediated proliferation was completely suppressed only by treating cells with specific inhibitors of both classes of enzymes. While four human PDE4 genes have been cloned, only three of the isoforms (PDE4A, B and D) have been identified in lymphocytes. Type 4 enzymes are specifically inhibited by rolipram [4-(3-cyclopentyloxy-4-methoxyphenyl)-2-pyrrolidone] (IC50=1 mMol/L) and the structurally related compound XX5 (IC50=2 mMol/L). U. Schwabe et al., "4-(3-cyclopentyloxy-4-methoxyphenyl)-2-pyrrolidone (ZK 62711): a potent inhibitor of adenosine cyclic 3',5'-monophosphate phosphodiesterases in homogenates and tissue slices from rat brain," *Molecular Pharmacology* 12:900 (1976). H. Sheppard et al., "Structure-activity relationships for inhibitors of phosphodiesterase from erythrocytes and other tissues," *Adv Cyclic Nucl Res* 1:103 (1972).

Theophylline induces apoptosis in CLL cells, but it is not a specific Type 4 inhibitor. Moreover, a clinical application of theophylline for CLL is complicated by its activity as an adenosine receptor antagonist. As an alternate approach, the present invention contemplates specific inhibitors.

C. Treating Patients

While the present invention is not limited by the nature of the prior treatment of the subject, it is contemplated that, in one embodiment, the present invention be utilized in patients who have not undergone prior treatment for their condition (ie., naive patients), as well as patients who have not responded to (or are refractory to) standard chemotherapeutic agents (e.g., alkylating agents). Thus, the present invention specifically contemplates treating patients who have failed standard therapy.

On the other hand, the present invention specifically contemplates the use of the inhibitors in combination with other drugs, including but not limited to cytotoxic drugs. This combination therapy is based on findings (described herein) that specific inhibitors can augment apoptosis when used with such drugs.

It is contemplated that the methods of the present invention be administered alone or can be administered with a pharmaceutical carrier selected on the basis of the chosen route of administration and standard pharmaceutical practice. In one preferred embodiment, the specific inhibitor is administered orally in solid dosage forms, such as capsules, tablets, or powders, or in liquid dosage forms, such as elixirs, syrups, and suspensions; however, it can also be administered parenterally, in sterile liquid dosage forms, or rectally in the form of suppositories.

One skilled in the art will be capable of adjusting the administered dose depending upon known factors such as the mode and route of administration; age, health, and weight of the recipient, nature and extent of symptoms, kind of concurrent treatment, frequency of treatment, and the effect desired. In one embodiment, the dosage is increased to overcome a non-responsive condition.

Additionally, the specific (and preferential) inhibitors of the present invention can be employed in admixture with conventional excipients, i.e., pharmaceutically acceptable organic or inorganic carrier substances suitable for parenteral (e.g., topical application) or enteral (e.g., oral) which do not deleteriously react with the active compounds.

Suitable pharmaceutically acceptable carriers include but are not limited to water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, merely to name a few. The pharmaceutical preparations can be sterilized and if desired mixed with auxiliary agents, e.g., lubricants, preservatives, stabilizers, wetting agents, emulsifier, salts for influencing osmotic pressure, buffers, coloring, flavoring, and/or aromatic substances and the like which do no deleteriously react with the active compounds. They can also be combined where desired with other agents, e.g., vitamins and/or antibiotics.

For enteral application, particularly suitable are tablets, liquids, drops, suppositories, or capsules. A syrup, elixir, or the like can be used wherein a sweetened vehicle is employed. Sustained or directed release compositions can be formulated, e.g., liposomes or those wherein the active compound is protected with differentially degradable coating, e.g., by microencapsulation, multiple coatings, etc.

In this manner, the present invention may be introduced into a subject in polymeric microspheres for the controlled release of the compound. Methods of producing microspheres from polymer can be found in U.S. Pat. No. 5,601,844 to Kagayama, et al., and U.S. Pat. Nos. 5,529,914 and 5,573,934 to Hubbel, et al., herein incorporated by reference.

Other medicaments can be produced in a known manner, whereby the known and customary pharmaceutical adjuvants as well as other customary carrier and diluting agents can be used. Examples include, but are not limited to, gelatins, natural sugars such as sucrose or lactose, lecithin, pectin, starch (for example cornstarch), alginic acid, tylose, talc, lycopodium, silica (for example colloidal silica), glucose, cellulose, cellulose derivatives for example, cellulose ethers in which the cellulose hydroxyl group are partially etherified with lower aliphatic alcohols and/or lower saturated oxyalchohols, for example, methyl hydroxypropyl cellulose, methyl cellulose, cellulose phthalate, stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil wheat germ oil, sunflower seed oil cod-liver oil), mono, di, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydricaliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane).

For injectable solutions or suspensions, non-toxic parenterally compatible diluting agents or solvents can be used, for example: Water, 1,3 butane diol, ethanol, 1,2-propylene glycol, polyglycols in a mixture with water, Ringer's solution, isotonic solution of sodium chloride or also hardened oils including synthetic mono or diglycerides or fatty acids like oleic acid.

Known and customary solution assistants or emulsifiers can be used in the production of the preparations. The following are examples of solution assistants and emulsifiers which can be used: Polyvinylpyrrolidone, sorbitan fatty acid esters such as sorbian trioleate, phosphatides such as lecithin, acacia, tragacath, polyoxethylated sorbitan monooleate and other ethoxyated fatty acid esters of sorbitan, polyoxyethylated fats, polyoxyethylated oleotriglycerides, linolized oleotriglycerides, polyethylene oxide condensation products of fatty alcohols, alkyl phenolene or fatty acids or also 1-methyl-3-(2-hydroxyethyl) imidazolidone-(2). The term polyoxyethylated means in this context that the substances in question contain polyoxyethylene chains whose polymerization is generally between 2 to 40 and especially between 10 to 20.

Furthermore, there can be added preservatives stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium-meta bisulfite, ascorbic acid, gallic acid, alkyl gallates, e.g., methyl gallate and ethyl gallate, butyl hydroxyanisole, nor-dihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

EXPERIMENTAL

The following example serves to illustrate certain preferred embodiments and aspects of the present invention and are not to be construed as limiting the scope thereof.

A. Reagents

The following reagents were obtained from commercial sources: alkaline phosphatase, cAMP, dibutyryl cAMP, calmodulin, forskolin (Sigma Chemical Co., St Louis, Mo.); vinpocetine (Alexis Biochemicals, San Diego, Calif.); recombinant human IL-2 (Genzyme, Boston, Mass.); F(ab')2 fragment goat anti-human IgG and IgM (Jackson Immunoresearch Laboratories, West Grove Pa.); Hoechst 33342 (Molecular Probes, Eugene, Oreg.). Rolipram (racemate of 4-[3'-cyclopentyloxy-4'-methoxyphenyl]-2-pyrrolidone) was a gift from Dr. Ronald Wohl, Berlex Laboratories (Wayne, N.J.).

B. Patient Selection

After IRB-approved informed consent, blood was drawn in heparinized tubes from patients with flow cytometry-verified CLL who were either untreated or at least one month post-chemotherapy. Patients with active infections or other serious medical conditions were not included in this study. Charts were reviewed to establish patients'sensitivity to chemotherapy and the stage of CLL. Resistance to a chemotherapeutic agent was defined as a rise in peripheral leukemic cell count or progression of adenopathy or splenomegaly prior to the initiation of the next scheduled cycle of chemotherapy.

C. Cell Purification and Culture

Mononuclear cells were obtained by density gradient centrifugation over Histopaque 1077 (Sigma Chemical Company, St. Louis, Mo.). As flow cytometry demonstrated that CLL cells made up more than 95% of the mononuclear cells so purified, both apoptosis and cAMP assays were performed with these patient cell preparations. For PCR experiments on CLL cells or for all experiments on normal circulating B cells, the whole mononuclear cells were further purified by incubation with Dynal anti-CD19 magnetic beads at a 1:1 bead:cell ratio, extensive washing with a magnetic particle concentrater and elution with CD19 Detachabead reagent (Dynal, Lake Success, N.Y.). Leukemic cells from two CLL patients showed sensitivity to rolipram-mediated apoptosis whether or not they were firther purified by anti-CD19 magnetic beads. Cells were cultured in RPMI 1640 media (Biowhittaker, Walkersville, Md.) supplemented with 10% fetal calf serum, 50 uMol/L 2-mercaptoethanol, 2 mnMol/L L-glutamine, 10 mMol/L Hepes pH 7.4, 100 U/mL penicillin, and 100 U/mL streptomycin (Sigma Chemical Company, St. Louis, Mo.) at 37° C. and 5% $CO_2$ in air.

D. RT PCR and Northern Analysis

RNA was isolated from CLL or whole mononuclear cells using Ultraspec reagent (Biotecx, Houston, Tex.). cDNA was synthesized from 10 ug of total RNA using oligo d(T) primers and Maloney murine leukemia virus reverse transcriptase in a final volume of 40 uL (Stratagene, La Jolla, Calif.). One mL of the first strand cDNA product was then used as template for PCR amplification with AmpliTaq DNA polymerase (Roche Molecular Systems, Branchburg, N.J.) by 40 thermocycles of 94° C. for 1 minute, 600° C. for 1 minute and 72° C. for 1 minute. The PDE PCR assay products were as follows with oligonucleotide sequences given 5'->3': Human PDE1B1 (Genbank accession # U56976) was 430 bp (1st base 1660; sense=GTC TTC ATT GAG TCC AAA GTG, antisense=GAC CTG CCA GCT AAG ATC TGG). Human PDE3A (cGIP1, HSPDE3B) (X95520) was 340 bp (1st base 2999, sense=GTA ACT CCT ATG ATG CTG CTG G, antisense=CTA TTC CTC TTC ATC TGC CTC). Of note, these PDE3 PCR oligonucleotides are selective for the human cGIP1 PDE, homologous to rat PDE3A, as the amplified sequence has only 50% nucleotide homology to the cardiac/platelet form of human PDE3 (cGIP2). Human PDE4A (M37744) was 461 bp (1st bp 1819, sense=GGA GGA AGA AAT ATC AAT GGC CC, antisense=GAT GTG TCC TCC CCA AAT GTC). Human PDE4B (L20966) was 479 bp (1st bp 2213, sense=ATT CTG AAG GAC CTG AGA AGG, antisense=CAG TGA GTT CAG TCA CTG TCG). For hybridization to Northern blots, these PCR products were subcloned into a plasmid vector (pCRII, Invitrogen, Carlsbad, Calif.) and subsequently utilized for PCR-based amplification of a32P dATP-labelled probes.

E. cAMP Assay

One million cells in 1 mL were treated for two hours with or without drugs. 0.8 mL of cells were pelleted by spinning at 4,000 rpm (RCF=1,310) in microcentrifuge tube. After discarding 0.7 mL, 400 uL of ethanol was added, vortexed and left on ice for five minutes. Particulate cell debris was removed by centrifugation at 14,000 rpm (RCF=16,000). The supernatant was stored at −20° C. until the day of assay, at which time it was dried in a Speedivac (Savant, Farmingdale, N.Y.) to a volume of 50 uL. After ten-fold dilution in 10 mMol/L Tris pH 8.0, 1 mMol/L EDTA, the cAMP sample was analyzed for cAMP concentration using a cAMP RIA kit (NEN, Boston, Mass.) according to the manufacturer's instructions using the nonacetylated protocol.

F. cAMP PDE Assay

The technique of Robiesek et al., itself adapted from an assay described by Thompson and Appleman, was used in modified form. S. A. Robicsek et al., "Multiple high-affinity cAMP-phosphodiesterases in human T-lymphocytes," *Biochem. Pharmacol.* 42:869 (1991). W. J. Thompson and M. M. Appleman, "Multiple cyclic nucleotide phosphodiesterase activities from rat brain," *Biochemistry* 10:311 (1991). 150 million purified CLL cells were pelleted and sonicated (Branson 350 Sonifier with micropit probe, output =2, 50% duty cycle) on ice in 1.0 mL of a buffer which contained 20 mMol/L Tris (pH 6.8), 1 mMol/L EDTA, aprotinin (50 u/mL), pepstatin (1 mg/mL), PMSF (1 mMol/L) and 3.75 mMol/L b-ME. Assay buffer contained 100 mMol/L Tris (pH 8.0), 20 mMol/l $MgCl_2$, 0.2% BSA and 7.5 mMol/L b-ME. [$^3$H]-cAMP (NEN, Boston, Mass.) was incubated with PDE for 10 minutes at 30° C. in 20 uL volumes (10 uL of sonication buffer and 10 uL of assay buffer) which contained 0.22 units of alkaline phosphatase. 10 uMol/L rolipram or 0.2 mMol/L calcium/20 nMol/L calmodulin were added to the assay buffer as appropriate. Reactions were halted by the addition of 0.5 mL of a 1:3 slurry w/v slurry of AG1-X8 anion exchange resin and a mixture of equal volumes of water and isopropanol. The resin bound the unreacted nucleotide but not the dephosphorylated nucleoside. Microcentrifuge tubes were spun at 3000 rpm (RCF=735) for 15 minutes. The radiolabelled nucleosides in the supernatant were counted using Ecoscint scintillation fluid (National Diagnostics, Atlanta, Ga.). Three to five enzyme dilutions were assayed to determine each velocity. Linearity of velocity with respect to enzyme concentration and time were verified.

G. DNA Ladder Gel Assay 10 million purified CLL cells were harvested by centrifugation following exposure to drugs during a 72 hour tissue culture incubation. Cells were lysed in 0.5 mL of 20 mMol/L Tris (pH 7.4), 0.4 mMol/L EDTA, 0.25% Triton X. After 15 minutes of incubation at room temperature, nuclei were removed by centrifugation at 14,000 rpm (RCF=16,000). The supernatant was transferred to a new tube and soluble DNA precipitated overnight at −20° C. following the addition of 55 mL of 5 Mol/L NaCl and 550 mL of isopropanol. After centrifugation at 14000 rpm for 10 minutes, followed by a 70% ethanol wash, the pellet was resuspended in 20 uL of 10 mMol/L Tris (pH 8.0), 1 mMol/L EDTA, 0.1 mg/mL RNase and incubated at 37° C. for 30 minutes prior to electrophoresis on 1.6% TBE agarose gels. DNA fragments were visualized by UV light after staining the gels with ethidium bromide.

H. Hoechst 33342 Apoptosis Assay

Hoechst 33342 was dissolved in water and frozen at 33 mg/mL at −20° C. One million cells/well were incubated in duplicate or triplicate in 48 well tissue culture plates (Costar, Cambridge, Mass.) with or without drug treatment for 48 hours in 1 mL of culture media. Cells were transferred to 12×75 mm polystyrene Falcon® 2054 FACS tubes (Becton Dickinson Labware, Lincoln Park, N.J.) and incubated for ten minutes at 37° C. with Hoechst 33342 at a final concentration of 0.25 mg/mL. 23 Cells were stored on ice until analysis on a FACS Vantage flow cytometer (Becton Dickinson, San Jose, Calif.). Hoechst 33342 dye fluorescence was excited with a UV laser and detected using a 450 bandpass filter; Data was analyzed using Cellquest software (Becton Dickinson, San Jose, Calif.).

EXAMPLE 1

This example describes the identification of PDE targets in CLL cells. As an initial approach to identify potential PDE targets in CLL, PCR was performed on cDNA derived from unpurified mononuclear cells of a CLL patient with oligonucleotides specific for human PDB1-1B, PDE3A, PDE-4A and PDE-4B, all of which have been previously identified in various normal and malignant primary lymphoid cells. Appropriate sized PCR products were detected from all four transcripts using this template. In order to reduce the likelihood of amplifying non-leukemic cell transcripts, we purified CD19-positive cells from this and two other CLL patients prior to synthesizing cDNA. PDE1-1B, PDE-4A and PDE-4B were still detected in these three templates, as they were in cDNA derived from normal whole mononuclear cells FIG. 1 shows that CLL cells contain transcripts for PDE 1B1, PDE4A and PDE4B. The cDNA utilized in the PCR in the bottom 3 panels was derived from leukemic cells from three different patients purified by positive selection for CD19 expression. The lowest band in the MWM lane on the left in the upper panel is 603 bp. Expected PCR product sizes for PDE1, 3A, 4A and 4B are 430, 340, 461 and 470 bp respectively.

Figure 2:
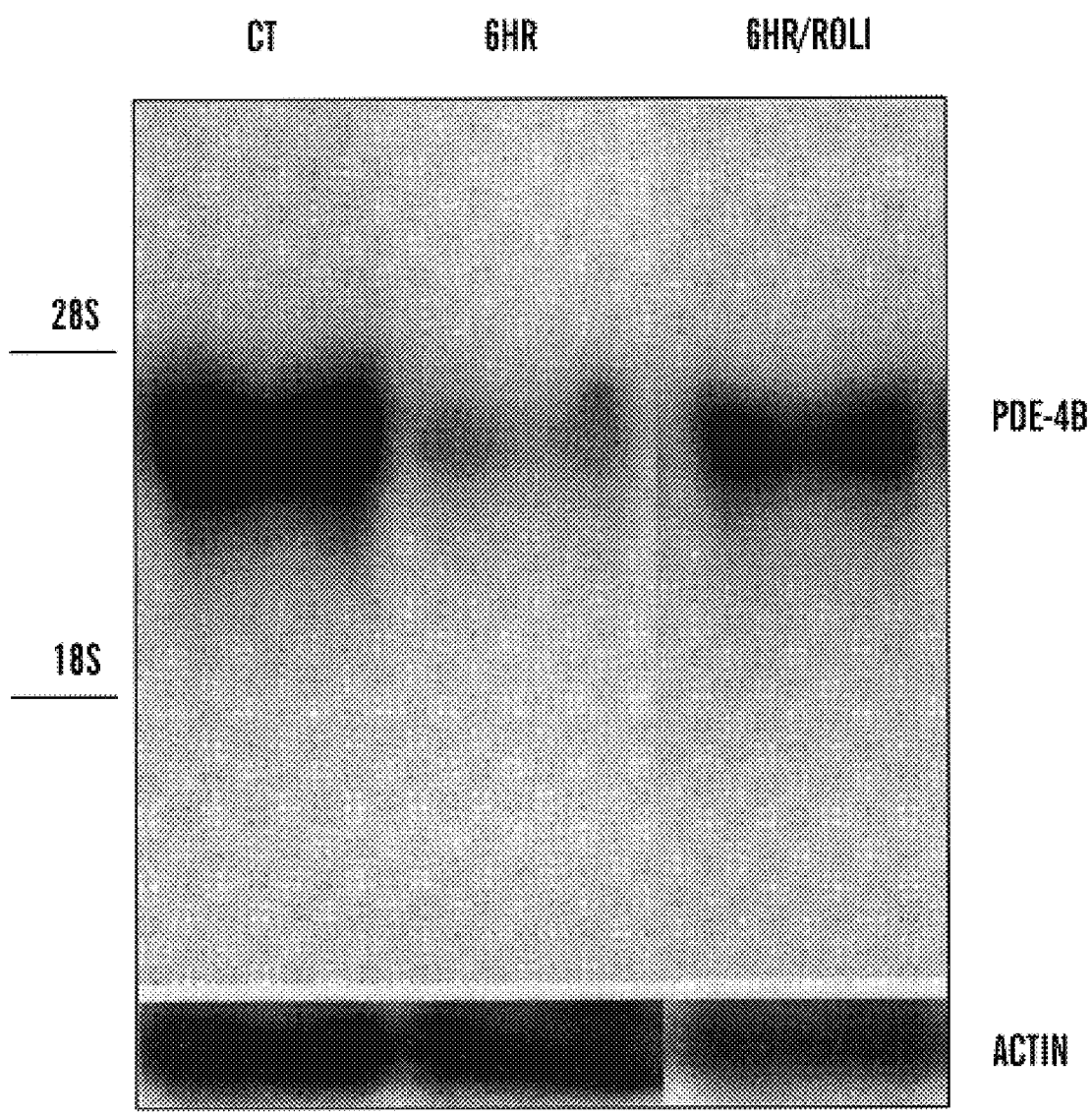
FIG. 2 is a Northern blot using the PCR products of FIG. 1.

Using the same four PCR products as probes on Northern blots, only PDE-4B transcript was detectable in 10 ug of loaded RNA. FIG. 2 shows that PDE4B levels fall in CLL cells following culture but are partially maintained by treatment with 10 uMol/L rolipram. RNA was isolated from 20 million CLL cells immediately after cell purification (CT), or after 6 hours culture in media alone (6 Hr) or with addition of 10 uMol/L rolipram (Roli). Equal loading and transfer of RNA was confirmed by hybridization with an actin probe as shown. These results are representative of Northern analysis performed on leukemic cells from two patients. PDE-4B transcript levels were significantly higher in freshly isolated CLL cells than in CLL cells which had been cultured for six hours. Addition of 10 uMol/L rolipram, a type 4 PDE-specific phosphodiesterase inhibitor, significantly reduced this fall in PDE-4B transcript levels during the six hour culture period.

EXAMPLE 2

Figure 3A:
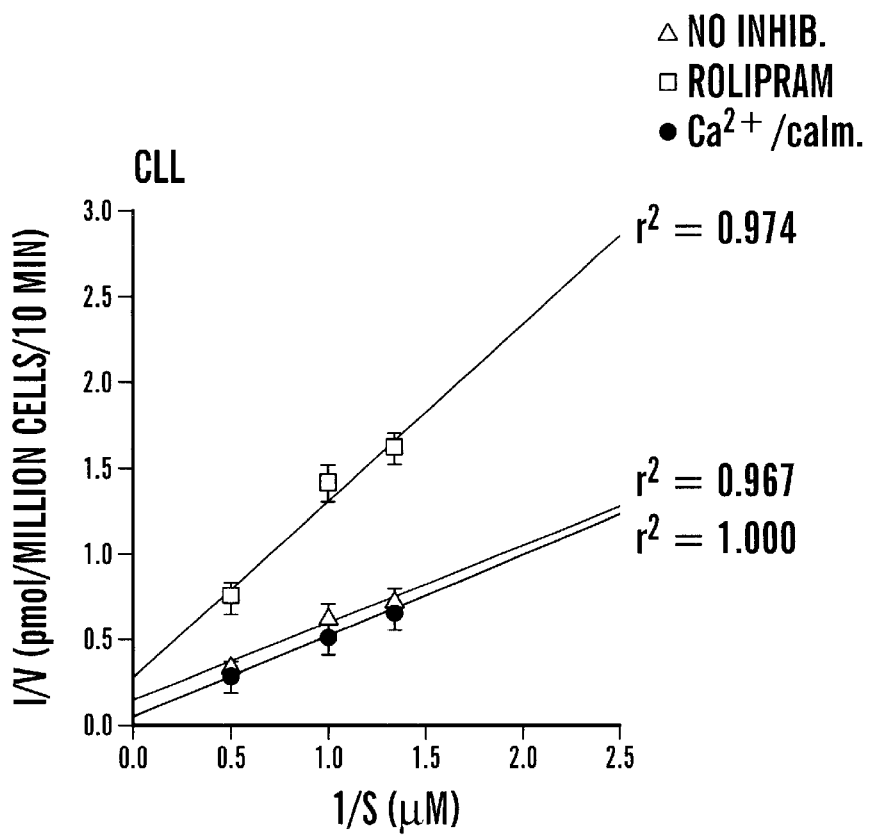
FIG. 3 graphically shows the PDE activity of CLL cells (left panel) and a murine B lymphoma cell line (right).
Figure 3B:
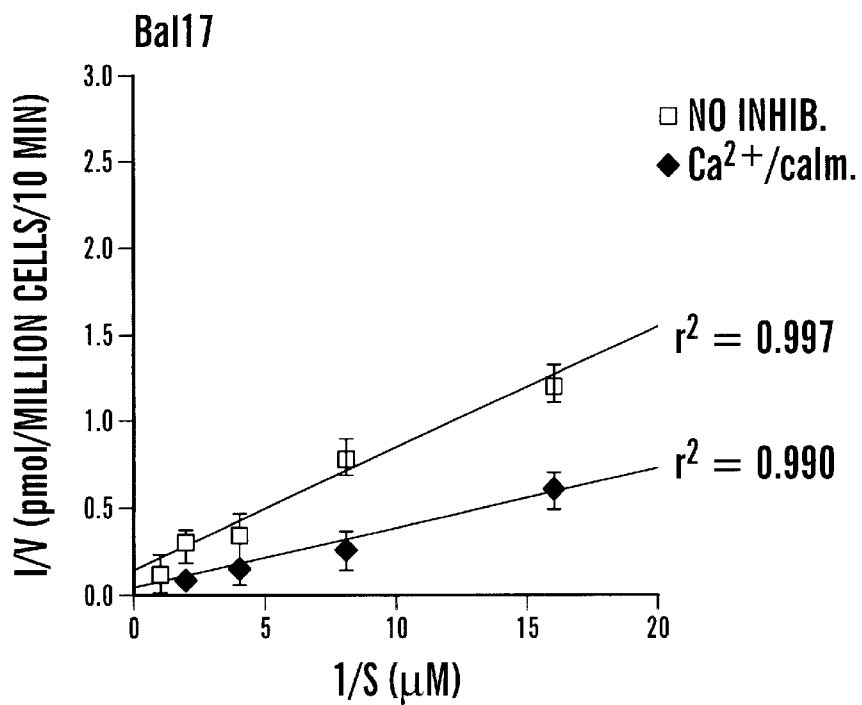
Figure 4C:
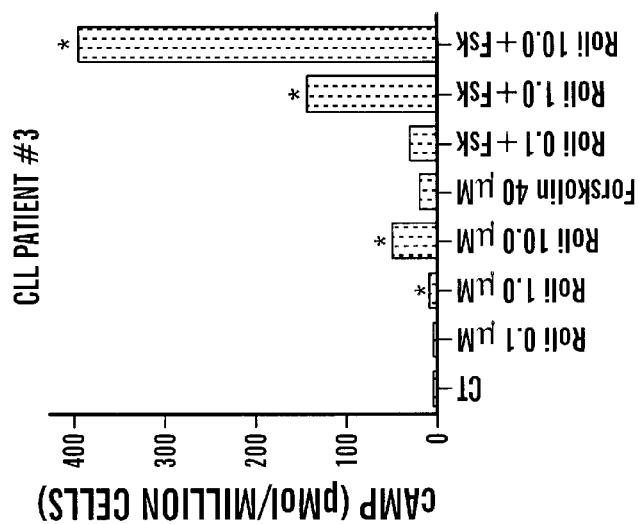
FIG. 4 graphically shows cAMP levels in CLL cells, WMC, and resting B cells.
Figure 4B:
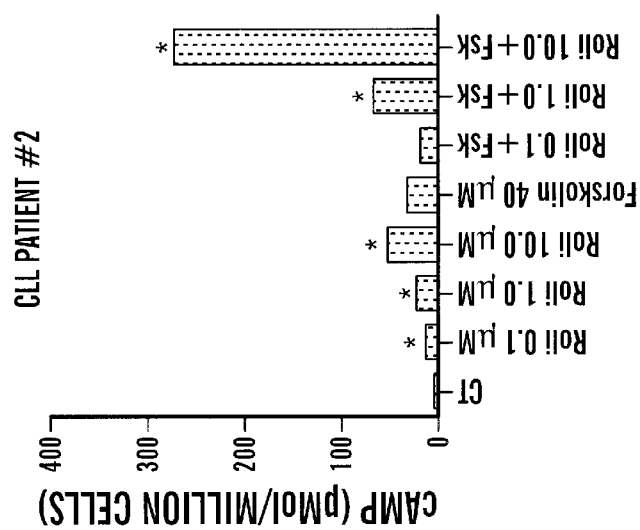
Figure 4A:
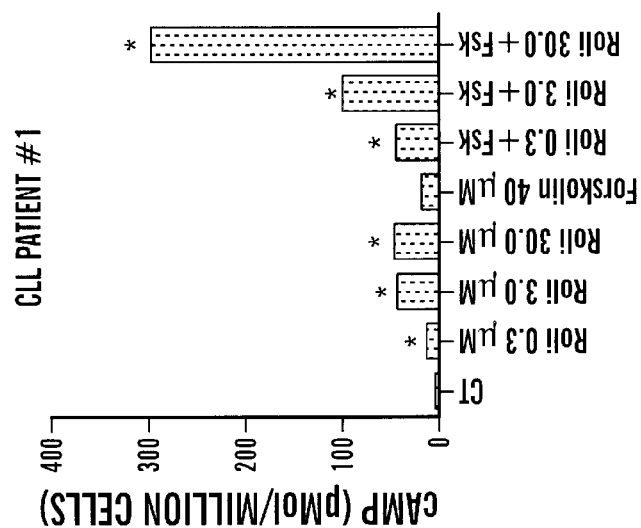
Figure 4F:
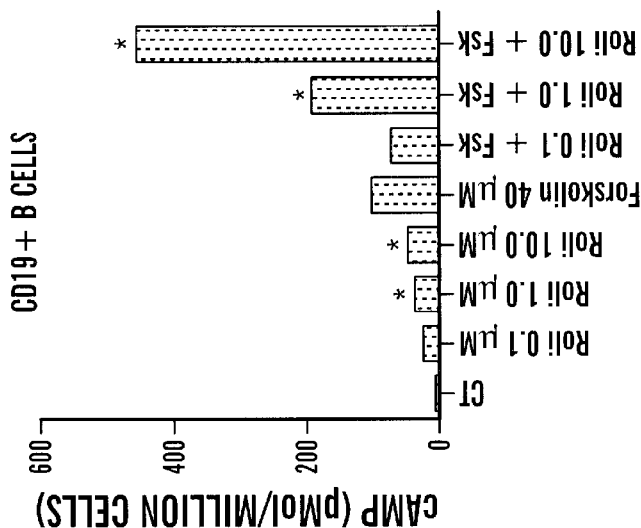
Figure 4E:
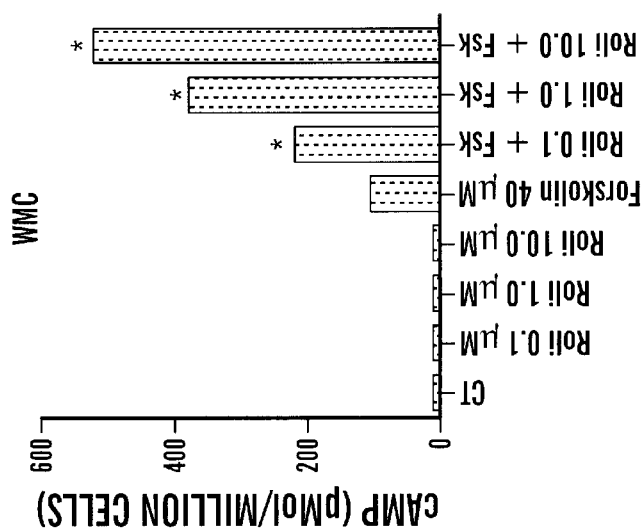
Figure 4D:
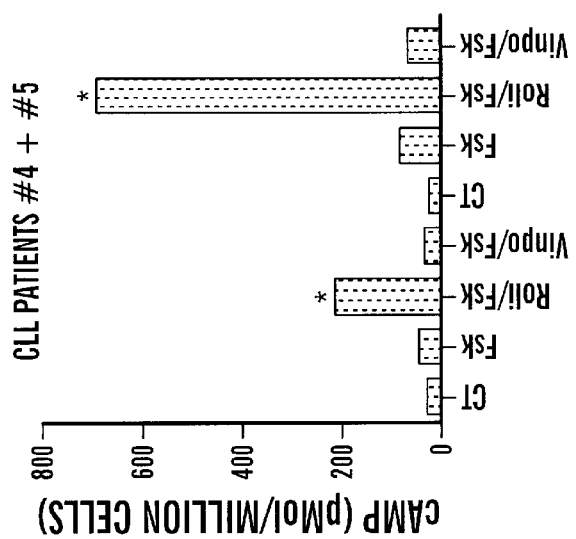

In this example, it was determined whether the above-described PDB transcripts were translated into protein with constitutive activity. PDE enzyme assays were performed on CLL cell lysates. FIG. 3 shows Lineweaver-Burk analysis of PDE enzymatic activity in lysates of CLL cells and Bal-17 cells (the CLL data are representative of enzymatic assays on three patients). Clearly, Type 1 and 4 PDE activity differs between a murine B lymphoma cell line (Bal-17) and CLL cells. We found no evidence of type 1 PDE activity in CLL cells as the basal PDE activity was not augmented by the addition of calcium and calmodulin (FIG. 3, left). PDE activity in CLL cells was inhibited by 10 uMol/L rolipram (rolipram altered both $K_m$ and the $V_{max}$, consistent with its known activity as a noncompetitive antagonist) but was not augmented by the addition of 0.2 mMol/L calcium and 20 nMol/L calmodulin. On the other hand, Bal-17 PDE activity is augmented by the addition of calcium and calmodulin (FIG. 3, right). That is to say, it was possible to identify substantial constitutive type 1 PDE activity in the murine B lymphoma cell line Bal-17, as demonstrated by a rise in PDE activity with the addition of calcium and calmodulin.

EXAMPLE 3

In this example, it was determined what role type 1 and type 4 PDE activity might play in the catabolism of cyclic nucleotides in CLL cells. cAMP levels were measured after culturing leukemic cells with varying concentrations of PDE-isoform specific inhibitors, either alone or in conjunction with an activator of adenylate cyclase, the diterpene forskolin. Specifically, one million freshly isolated cells were incubated with the indicated drugs for two hours prior to analysis of cAMP in cell lysates using a radioimmunoassay. The results are shown in FIG. 4 and the data are the mean of three individually assayed culture wells. The experimental conditions indicated with an asterisk had a greater [cAMP] than, as appropriate, the untreated or forskolin-treated control cells (t test: one-tailed significance level <0.05).

In panel D, vinpocetine was added at 30 uMol/L. When incubated with forskolin and the PDE-1 inhibitor vinpocetine, CLL cell cAMP was not augmented above levels induced by forskolin alone (FIG. 4, panel D). Incubation of Bal-17 cells with vinpocetine reduced both basal and forskolin-stimulated cAMP levels, a result in keeping with the reported primary effect of this drug on cGMP rather than cAMP levels (data not shown). In contrast, addition of the type 4 PDE inhibitor rolipram augmented CLL cAMP levels, both when used alone and more dramatically when combined with forskolin (FIG. 4, Panels A–D). CLL cells were not unique with respect to their response to these isoform-specific inhibitors. cAMP levels in both a predominantly T cell population (IL-2 supplemented normal whole mononuclear cells; >90% CD3+ T cells by flow cytometry) and magnetic-bead purified CD19+ B cells rose following inhibition of type 4 but not type 1 PDE activity (FIG. 4, Panels E and F and data not shown).

EXAMPLE 4

Figure 5:
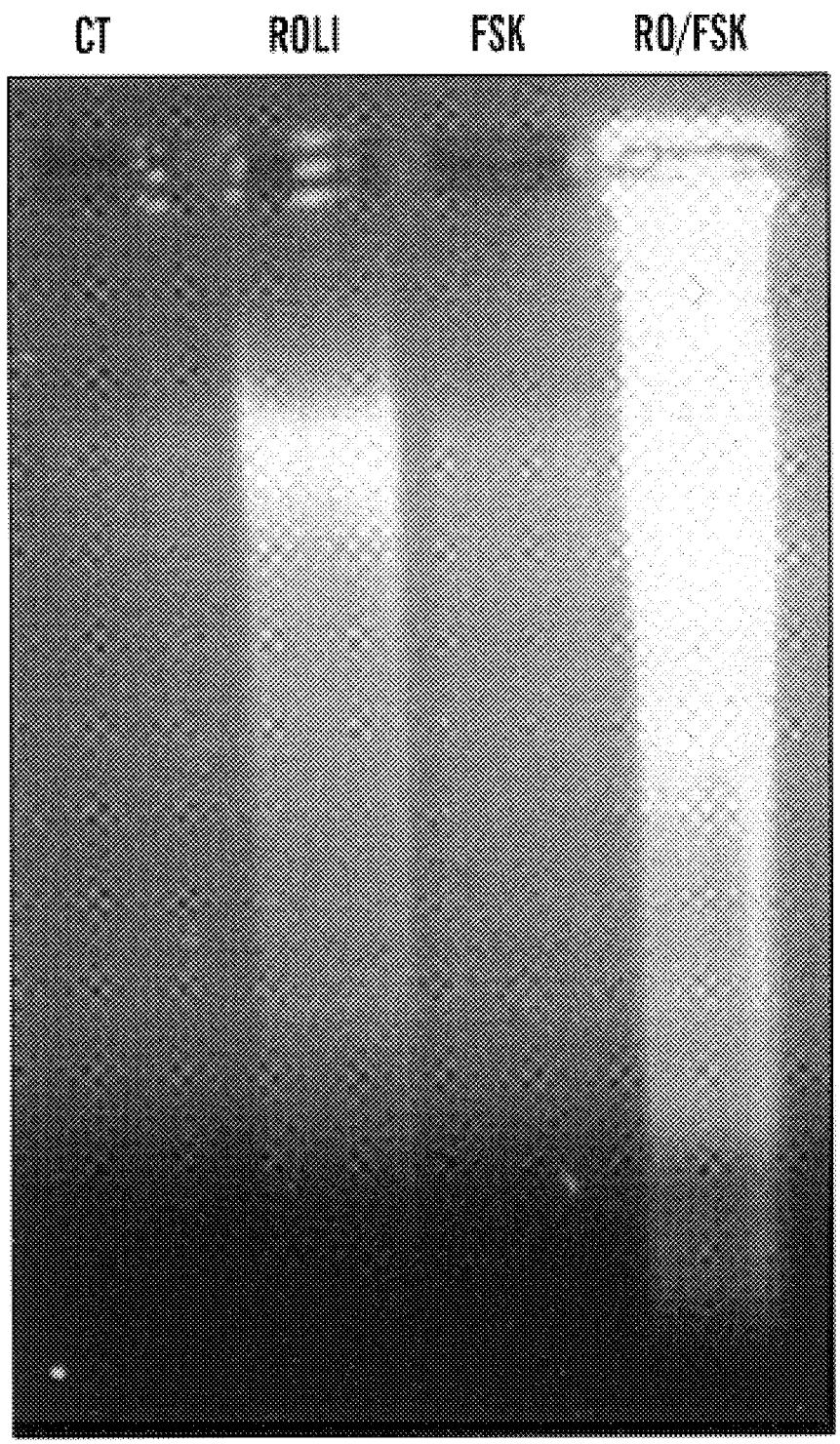
FIG. 5 shows the DNA fragmentation results on gel electrophoresis using a 1.5% agarose gel wherein the bands are visualized with ethidium bromide.

This example demonstrates that Type 4 PDE inhibition induces CLL apoptosis The above-described results identified the type 4 cAMP phosphodiesterase family as an important regulator of cAMP levels in CLL cells. Consequently, a study of the activity of type 4-specific PDE inhibitors as inducers of cAMP-mediated apoptosis in leukemic cells from CLL patients was carried out. CLL cells were incubated for 72 hours either alone or with 10 uMol/L rolipram, 40 uMol/L forskolin or both agents. We tested whether rolipram induces internucleosomal DNA fragmentation characteristic of apoptosis by isolating soluble DNA from the leukemic cells with detergent treatment, then removing DNA from intact non-apoptotic nuclei by centrifugation. Specifically, soluble DNA was isolated from ten million CLL cells cultured for 72 hours in media (CT), 10 uMol/L rolipram (Roli), 40 uMol/L forskolin (Fsk) or a combination of the latter two agents (Ro/Fs). DNA fragments were resolved by electrophoresis on a 1.5% agarose gel and visulized with ethidium bromide. FIG. 5 shows the results. These data are representative of the four leukemic cell samples tested. As shown in FIG. 5, while culture of CLL cells in media alone resulted in only a faint DNA "ladder", treatment with rolipram and/or forskolin resulted in pronounced internucleosomal DNA fragmentation.

Figure 6:
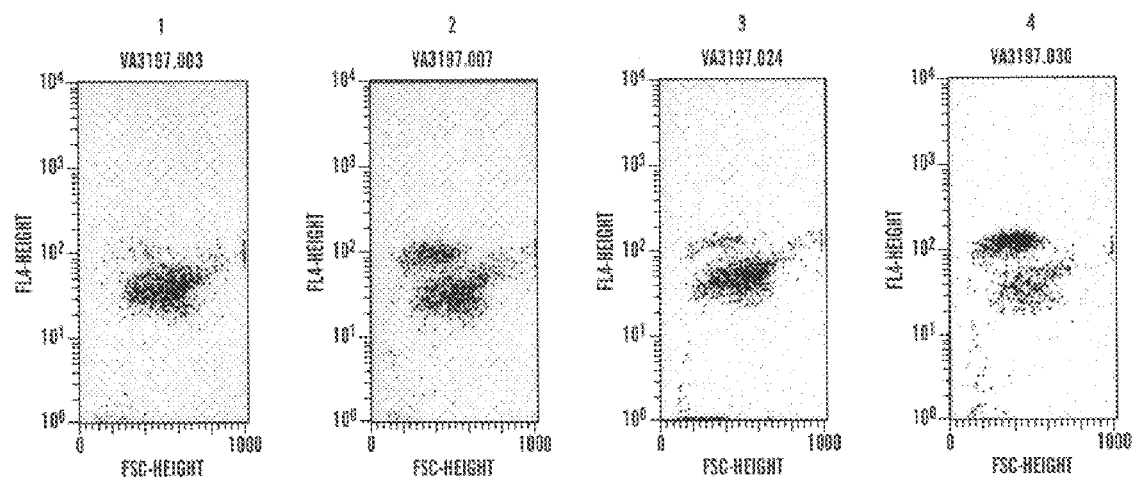
FIG. 6 shows the results of Hoechst 33342 flow cytometry.
Figure 7B:
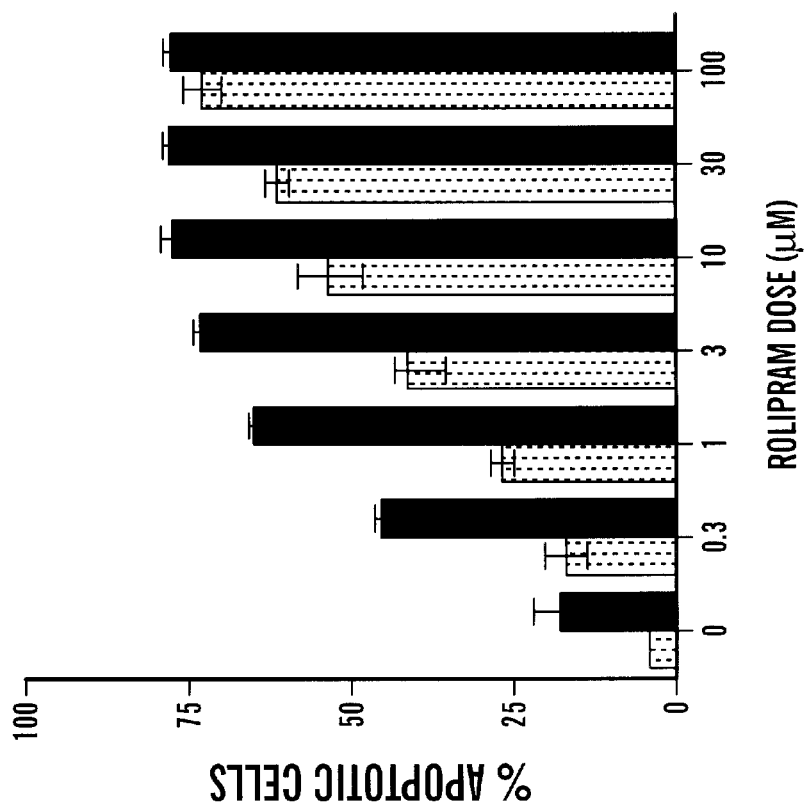
FIG. 7 graphically shows the increasing percent of apoptotic cells as a function of time and rolipram dose.
Figure 7A:
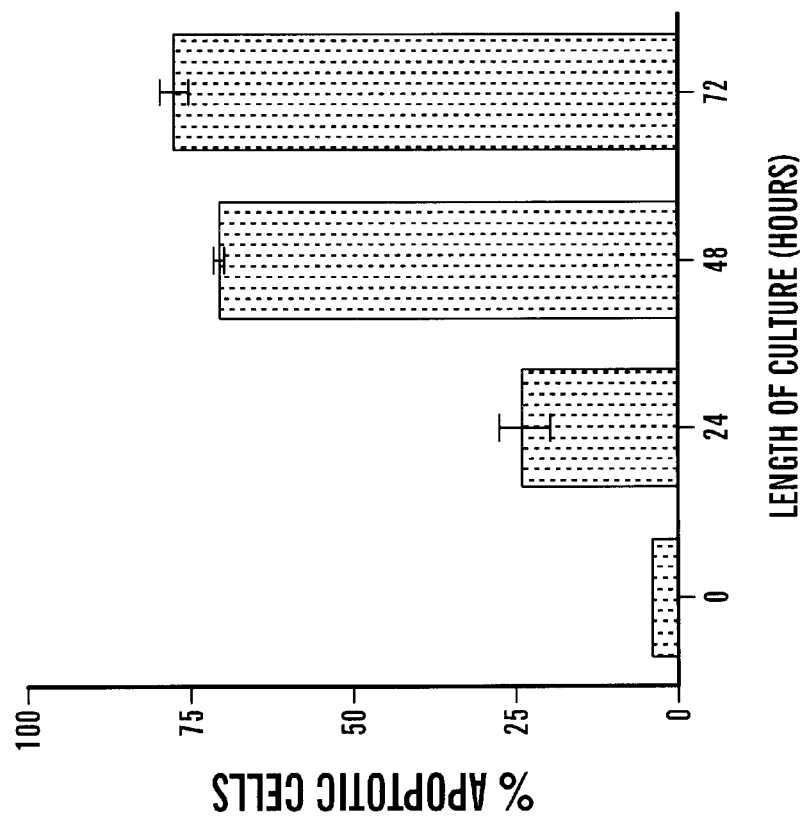

As a more quantitative analysis of CLL apoptosis, we utilized a flow cytometry method in which apoptotic cells are distinguished both by their reduced size (FSC) and their increased uptake of the lipophilic UV fluorescent dye Hoechst 33342 (FL-4) when the intact, heterogeneous cell population is incubated with a low concentration of the dye (0.25 ug/mL) for 10 minutes at 37° C. Specifically, cells were cultured for 72 hours in media (1), 1uMol/L rolipram (2), 40 uMol/L forskolin (3) or a combination of the two drugs (FIG. 6). The abcissa reflects forward light scatter and the ordinate Hoechst 33342 fluorescence. Apoptotic cells are characterized by reduced forward light scatter and increased Hoechst 33342 fluorescence. Previous reports of cAMP induced lymphoid apoptosis have noted that this form of programmed cell death may take 48 to 72 hours to develop maximally. Using the Hoechst 33342 assay in a time course experiment, we found that the combination of 10 uMol/L rolipram and 40 uMol/L forskolin induced significant CLL apoptosis which plateaued 48 to 72 hours after the addition of these drugs (FIG. 7, left panel). CLL cells were cultured for 72 hours in one mL of media with the indicated concentration of rolipram with (black bars) or without (stippled bars) the addition of 40 uMol/L forskolin. Using the 72 hour culture period, we found a dose dependent increase in CLL cell apoptosis when leukemic cells were incubated with rolipram (FIG. 7, right panel). Treatment of CLL cells with forskolin alone induced moderate apoptosis, but combination of forskolin with even low doses of rolipram resulted in a supra-additive effect on induction of CLL apoptosis (FIG. 7, right panel). Similar results were obtained with a structurally distinct PDE4 inhibitor, XX5, or when isoproterenol or prostaglandin E2 were utilized to activate CLL adenylate cyclase rather than forskolin (data not shown).

When CLL cells were incubated with the type 1 PDE inhibitor, vinpocetine, they underwent apoptosis at dosages of 10 or 30 uMol/L but not at 2 uMol/L. Given that vinpocetine failed to augment cAMP accumulation and that we were unable to detect type 1 PDE activity in CLL cells, we suspect that this drug may induce apoptosis by a mechanism unrelated to cAMP. Consistent with this hypothesis, the kinetics of CLL apoptosis were different when vinpocetine was utilized with peak apoptosis by 24 rather than 48 hours (data not shown). Nonetheless, we cannot rule out either a temporally restricted or a topologically compartmentalized cAMP-mediated apoptotic effect from this drug.

Given that CLL is a clinically heterogeneous disease, we tested a total of 14 CLL patients of varying clinical stage, treatment history and known resistance to chemotherapeutic agents for the sensitivity of their cells to phosphodiesterase inhibitor-mediated apoptosis. Patients were assessed for the apoptotic sensitivity of their leukemic cells to rolipram, forskolin or both drugs. In samples from ten "rolipram-sensitive patients", treatment with 10 uMol/L rolipram induced apoptosis in more than a third of the leukemic cells, with overall apoptosis ranging from 44 to 80% (see Table 1 for tabulated results). Among the seven rolipram-sensitive patients whose cells were treated with both conditions, 40 uMol/L forskolin as a single agent induced less apoptosis than rolipram alone, suggesting that blockade of cAMP catabolism induced a more potent apoptotic signal than further augmentation of adenylate cyclase activity (p<0.08, Wilcoxon signed-ranks test for matched pairs). Among four relatively rolipram-resistant patient samples (Pt #'s 11–14: Table 1), the absolute increase in apoptotic cells was less than 33%, with overall apoptosis ranging from 14 to 40%. Nonetheless, addition of forskolin to rolipram augmented apoptosis (68% and 69%) in two of the three patient samples examined within this group.

TABLE 1

| Pt. | Rai | Drug Res. | Basal | Roli | Fsk | R/Fs | dbcAMP |
|---|---|---|---|---|---|---|---|
| 1. | III | — | 47 | 80 | ND | ND | ND |
| 2. | IV | Ch, Cy | 18 ± 2 | 79 | 46 | 89 | ND |
| 3. | IV | Ch, CH | 38 | 77 ± 1 | 59 ± 0 | 79 ± 1 | 71 ± 3 |
| 4. | I | — | 31 ± 2 | 76 ± 2 | ND | ND | ND |
| 5. | IV | — | 18 | 57 ± 2 | ND | ND | ND |
| 6. | IV | Ch | 17 ± 4 | 54 ± 1 | 30 ± 4 | 60 ± 2 | 39 ± 4 |
| 7. | II | Ch | 13 ± 2 | 47 ± 2 | 32 ± 0 | 58 ± 0 | 32 ± 4 |
| 8. | 0 | — | 5 | 46 | 22 | 55* | ND |
| 9. | IV | Ch, Cy, Fl | 4 ± 0 | 44 ± 3 | 17 ± 4 | 77 ± 2 | 46 ± 1 |
| 10. | I | — | 11 | 44 ± 0 | 26 ± 4 | 56 ± 0 | ND |
| 11. | 0 | — | 24 ± 4 | 40 ± 0 | 40 ± 3 | 69 ± 0 | 39 ± 2 |
| 12. | IV | Ch, Fl, 2C | 0 ± 4 | 38 ± 1 | 43 ± 1 | 68 ± 0 | ND |
| 13. | 0 | — | 2 ± 0 | 34 ± 0 | ND | ND | 23 ± 6 |
| 14.** | I | — | 13 ± 0 | 14 ± 0 | 19 ± 3 | 37 ± 3 | 22 ± 0 |

Apoptosis of CLL patients' leukemic cells following treatment with 10 uMol/L rolipram, 40 uMol/L forskolin or 100 uMol/L dbcAMP. Cultures were performed for three days and the percentage of apoptotic cells measured by Hoechst 3342 flow cytometry.
Drugs: Ch = chlorambucil, CH = CHOP, Cy = cyclophosphamide, Fl = fludarabine, 2C = 2-chlorodeoxyadenosine.
SEMs are shown for samples done in triplicate; the remainder of the values are the mean of duplicate cultures.
*Rolipram was at 1 uMol/L.
**This patient had a significant population of cells with prolymphocyte morphology.

EXAMPLE 5

Figure 8A:
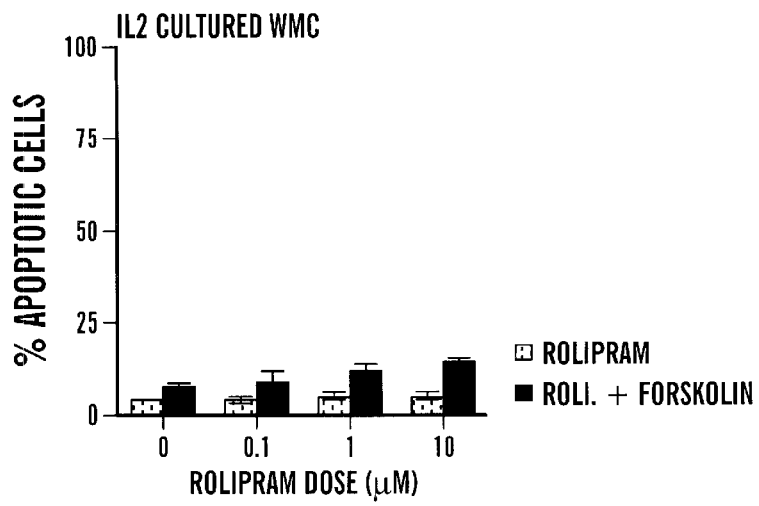
FIG. 8 graphically shows the different sensitivity of various cells to the specific inhibitors of the present invention.
Figure 8B:
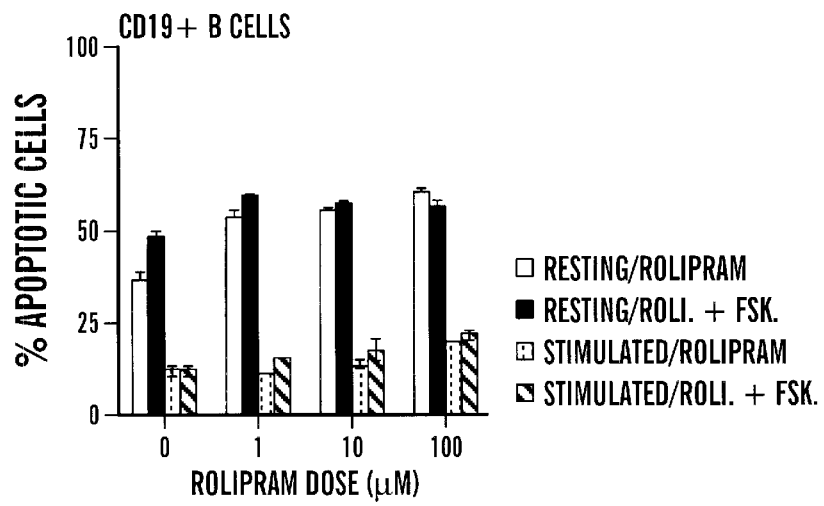
Figure 8C:
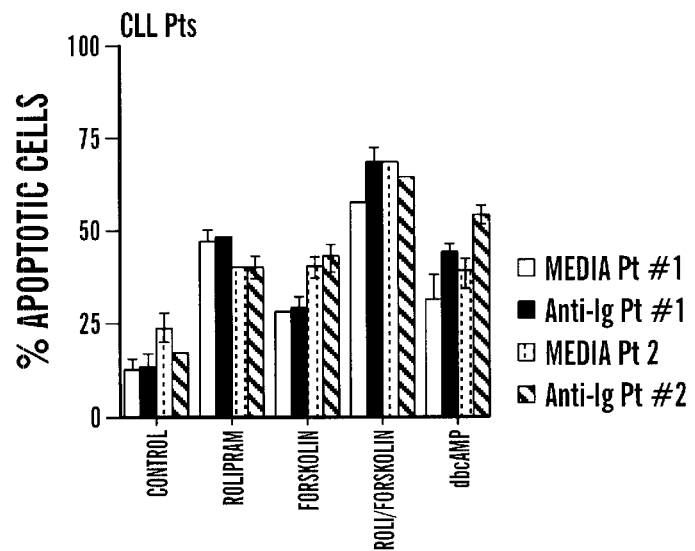

This example describes the effect of PDE4 inhibition on normal B and T cells. Given that cAMP has been reported to be cytocidal to specific normal lymphocyte subsets, it was determined whether rolipram also induced apoptosis in normal circulating human B and T cell populations. Specifically, one million WMC were cultured with the indicated concentration of rolipram with or without the addition of 40 uMol/L forskolin for 72 hours in the presence of 2 units/mL IL-2. Apoptosis was determined by Hoechst 33342 flow cytometry. It was found that IL-2 cultured WMC (>90% CD3+ T cells by flow cytometry) were resistant to even high doses of rolipram and forskolin (FIG. 8, upper panel). In contrast, magnetic bead purified CD19+B cells were sensitive to rolipram, although the increment in apoptosis observed was superimposed on a high basal apoptosis rate that has previously been reported in cultured human B cells. Given that crosslinking of cell surface immunoglobulin on resting B cells has been reported to reduce basal and forskolin-induced apoptosis in culture, we also stimulated CD19+ cells with a polyclonal Fab'2 anti-IgM/IgG reagent 30 minutes prior to the addition of the phosphodiesterase inhibitor. Prior stimulation through surface Ig markedly reduced both basal apoptosis and the sensitivity of the B cells to rolipram (FIG. 8, middle panel). In contrast, anti-Ig stimulation of CLL cells derived from two patients failed to protect these cells from rolipram-induced apoptosis, a result that is consistent with reported defects in CLL cells in either surface m heavy chain expression or mutations in the B29 (CD79b) B cell receptor accessory protein (FIG. 8, bottom panel).

Figure 9A:
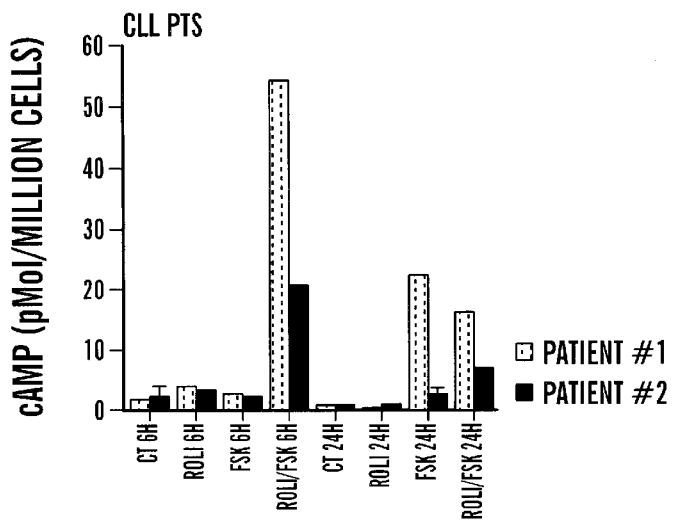
FIG. 9 graphically shows that rolipram blocks cAMP catabolism in both sensitive and resistant lymphoid populations.
Figure 9B:
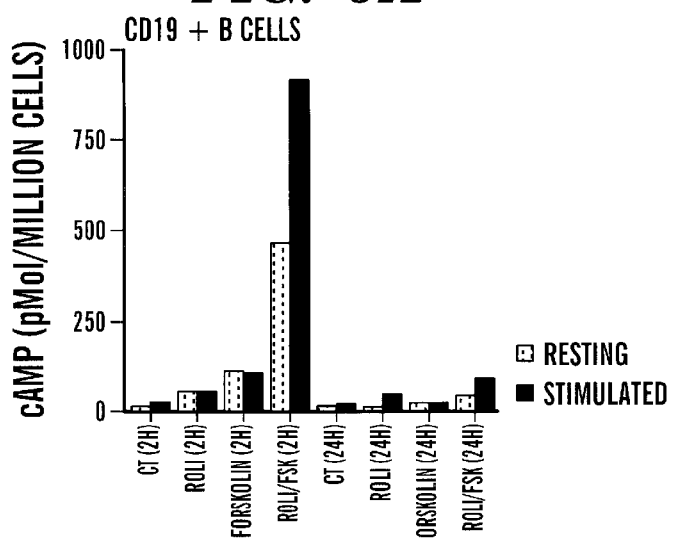
Figure 9C:
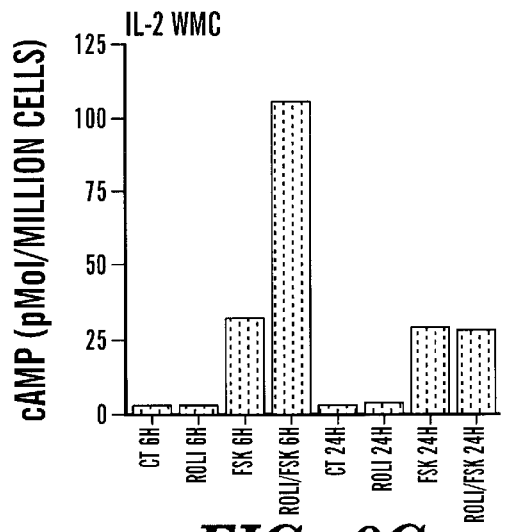

The alteration in rolipram sensitivity in anti-Ig stimulated B cells was not due to a change in the ability of this drug to augment cAMP levels at two hours in these cells, as rolipram raised cAMP levels equivalently in unstimulated or stimulated CD19+ B cells (FIG. 9). In order to determine whether the rolipram-sensitive cell populations had a more prolonged elevation of cAMP than the insensitive cell populations following drug treatment, we measured cAMP levels 6 or 24 hours after addition of rolipram, times at which levels of apoptosis were still low even in sensitive populations. For each of the four cell populations, two or six hours after drug treatment, cAMP levels were higher for rolipram/forskolin-treated cells than for forskolin only treated cells (test: one tailed significance level<0.05) (FIG. 9). By 24 hours, there was no longer significant rolipram-induced augmentation of forskolin-stimulated cAMP accumulation in any of the four cell populations (FIG. 9). Thus, the degree of cAMP augmentation by rolipram did not predict the sensitivity of cell populations to induction of apoptosis by this drug at any time point tested.

EXAMPLE 6

Figure 10:
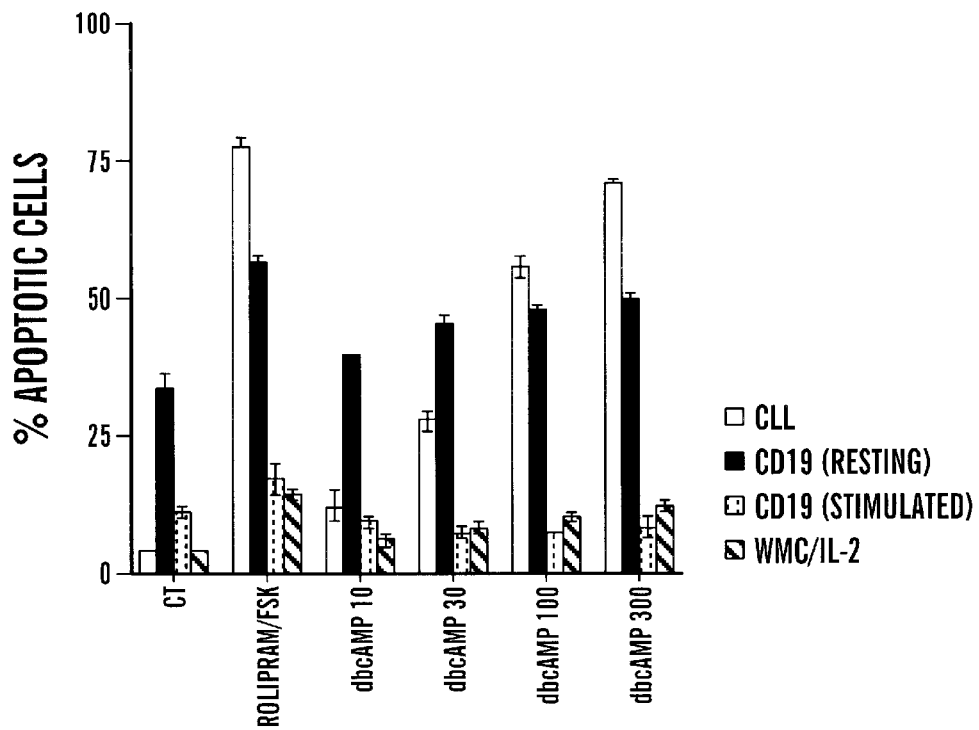
FIG. 10 graphically shows that sensitivity to rolipram mirrors the sensitivity to dbcAMP.

In this example, the sensitivity of four populations to the cell permeable cAMP analog, dibutyryl cAMP was examined. Specifically, 1 million CLL cells, resting or anti-Ig activated CD19+ cells, or IL-2 supplemented WMC were cultured for 72 hours with 10 uMol/L rolipram, 40 uMol/L forskolin or the dbcAMP concentration indicated in FIG. 10 (in uMol/L) prior to measurement of apoptosis by Hoechst 33342 flow cytometry. The SEMs of tiplicate cultures are indicated. As shown in FIG. 10, a strong correlation was found between rolipram and dbcAMP induced apoptosis. For CLL cells and resting B cells, the percentage of apoptotic cells increased significantly relative to control cells after treatment with rolipram and forskolin or concentrations of dbcAMP greater than or equal to 30 mMol/L (t test: one tailed significance level <0.05). For anti-Ig stimulated B cells or IL-2 cultured WMC, comparable treatments did not significantly increase the percentage of apoptotic cells. Consistent with these results, in the seven CLL patients studied thus far, there has also been a correlation between sensitivity to rolipram and sensitivity to dbcAMP (see Table 1). These data indicate that type 4 PDE is the relevant target for rolipram in its induction of apoptosis in CLL cells.

EXAMPLE 7

Figure 11:
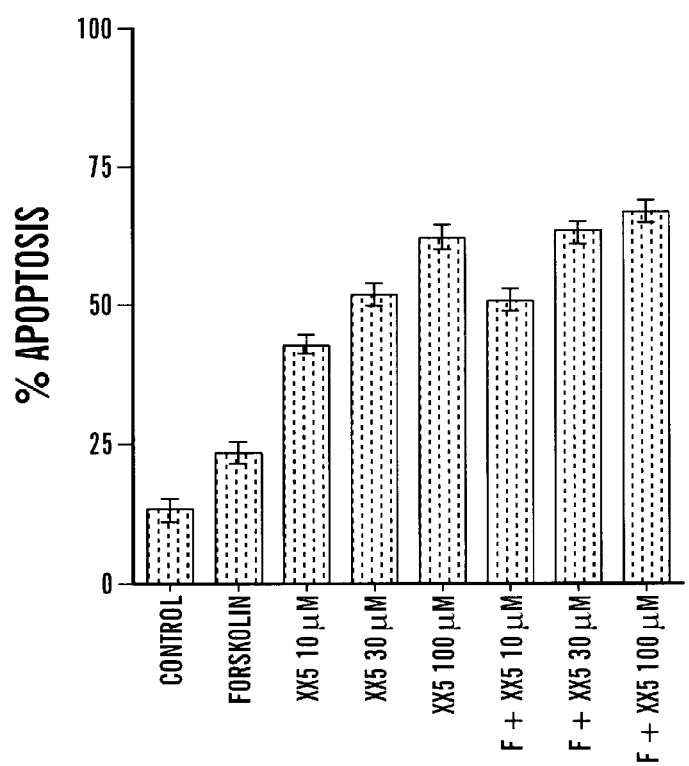
FIG. 11 graphically shows an increase in the percent apoptotic cells with increasing doses of the inhibitor XX5.

It is not intended that the present invention be limited to only one particular inhibitor. The present invention contemplates the treatment of patients with chronic lymphocytic leukemia (CLL) with a variety of inhibitors that specifically inhibit Type 4 cyclic adenosine monophosphate phosphodiesterase. For example, FIG. 11 graphically shows an increase in the percent apoptotic cells with increasing doses of the inhibitor XX5. One million purified CLL cells were cultured for three days in media (control), 40 uM forskolin (F) and/or the indicated concentrations of the PDE4 inhibitor XX5. Cells were then harvested and analyzed for apoptosis using the Hoechst 33342 FACS assay. SEM of triplicate cultures is shown.

EXAMPLE 8

In this example, it is demonstrated that the specific inhibitors of the present invention augment apoptosis induced by commonly used drugs (e.g., doxorubicin, chlorambucil and fludarabine). FIG. 12 graphically shows that rolipram augments fludarabine-induced apoptosis in CLL cells. One million CLL cells were incubated for three days in the presence of media (control), theophylline (50 ug/mL), forskolin (40 uMol/L), rolipram (10 uMol/L), fludarabine (0.3–3.0 uMol/L) or combinations of these drugs. The percentage of apoptotic cells was determined by Hoechst 33342 FACS analysis. SEM of triplicate cultures is shown. The right and left graphs represent data derived from the cells of two different CLL patients.

Figure 13:
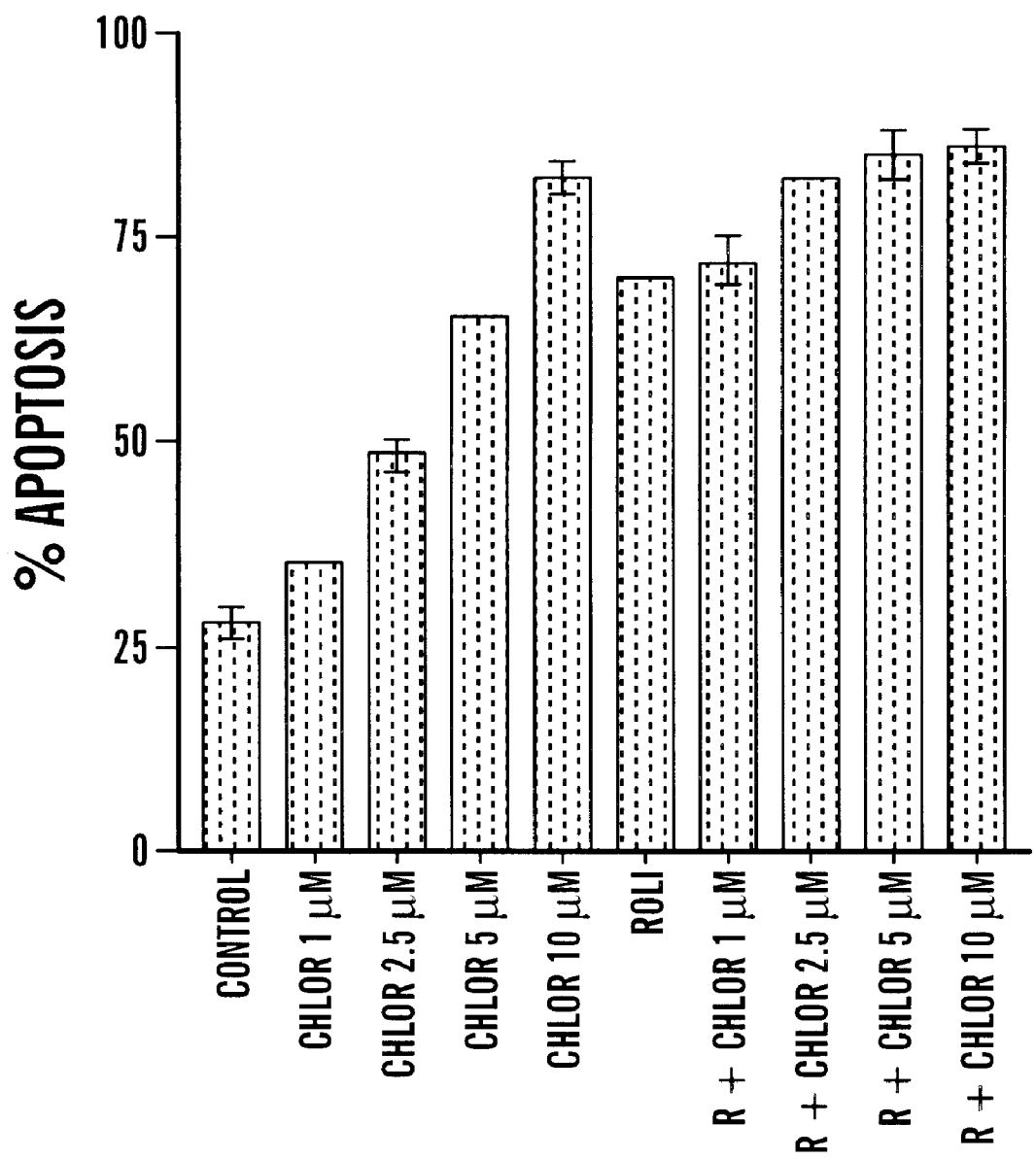
FIG. 13 graphically shows that rolipram augments chlorambucil-induced apoptosis in CLL cells.

FIG. 13 graphically shows that rolipram augments chlorambucil-induced apoptosis in CLL cells. CLL cells were incubated for three days with media (control), chlorambucil (indicated concentration in uMol/L), rolipram (10 uMol/L) or a combination of chlorambucil and rolipram. The percentage of apoptotic cells was then determined by Hoechst 33342 FACS analysis. SEM of triplicate samples are shown.

Figure 14:
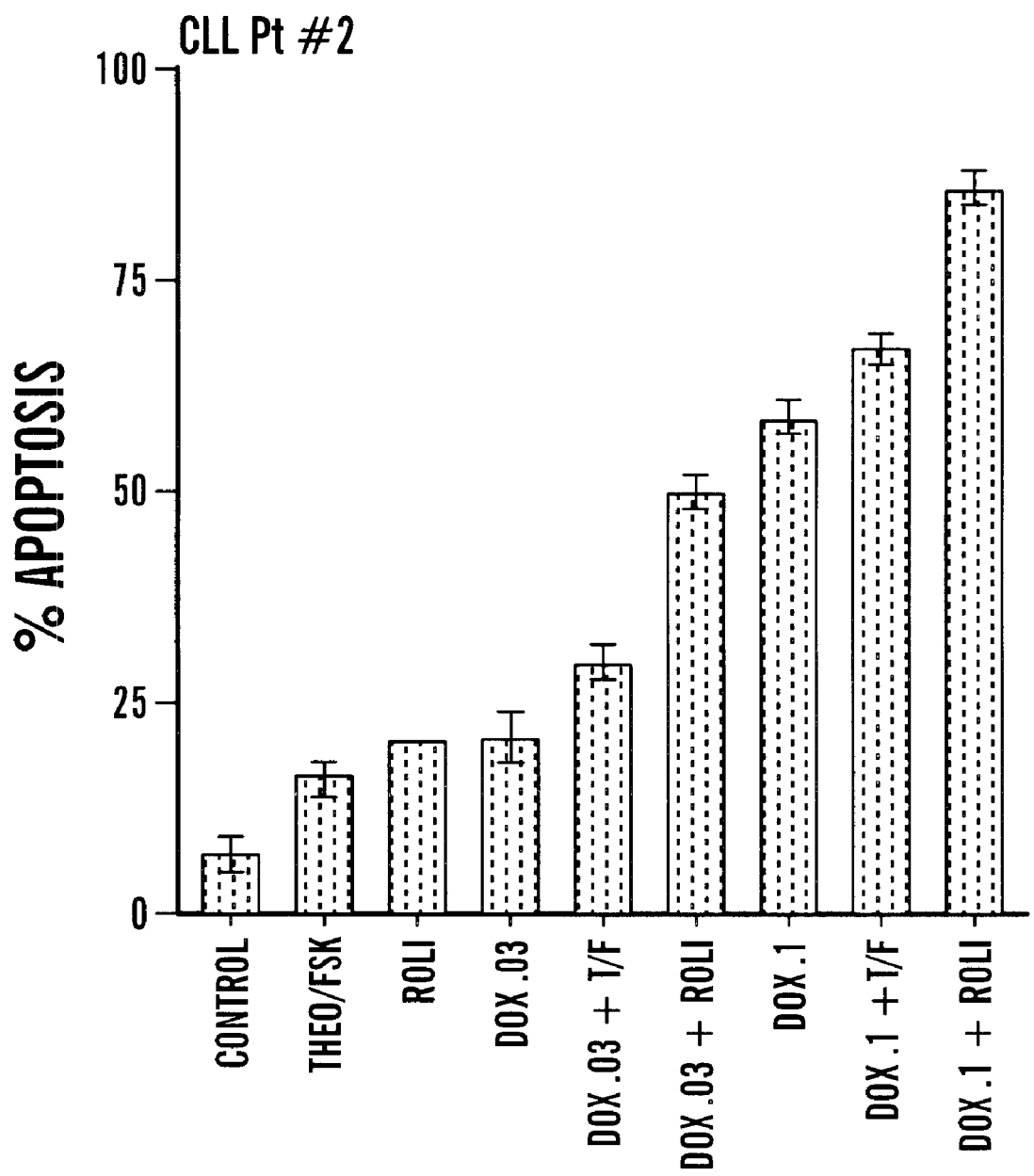
FIG. 14 graphically shows that rolipram augments doxorubicin-induced apoptosis in CLL cells.

FIG. 14 graphically shows that rolipram augments doxorubicin-induced apoptosis in CLL cells. One million CLL cells were cultured for three days with theophylline (50 ug/mL), rolipram (10 uMol/L), forskolin (F: 40 uMol/L), doxorubicin (0.03 or 0.1 uMol/L) or combinations of these drugs as indicated. The percentage of apoptotic cells was determined by Hoechst 33342 FACS analysis. SEM of triplicate cultures is shown. Consequently, the present invention specifically contemplates the use of the inhibitors in combination with other drugs, including but not limited to cytotoxic drugs.

From the above, it should be clear that, inhibition of type 4 cAMP phosphodiesterase activity is a novel means by which to trigger apoptosis in chronic lymphocytic leukemia cells in vitro. Treatment of CLL cells with the PDE4 family-specific inhibitor rolipram raised cAMP levels and induced apoptosis in a dose and time-dependent manner, an effect which correlated with apoptosis induced by dbcAMP. Treatment is possible even where patients demonstrated clinical resistance to chlorambucil, cyclophosphamide and/or fludarabine (see Table 1).

If PDEs are to be a useful pharmacologic target in the therapy of CLL, drug dosages which trigger apoptosis in leukemic cells in vivo must have clinically tolerable effects on other tissues. Despite their widespread tissue distribution, type 4 inhibitors have been used effectively as anti-inflammatory drugs in animal models of asthma, inhibiting pulmonary eosinophil accumulation after allergen challenge of sensitized animals. Rolipram has been studied extensively as an antidepressant in humans and is well tolerated, although higher dosages are emetogenic.

An effort has been made here to determine whether rolipram's ability to induce apoptosis in the leukemic cells of some CLL patients is unique to this malignant population or shared by normal circulating lymphocytes. We observed that IL-2 cultured WMC and sIg-triggered B cells were largely insensitive to both rolipram and dbcAMP-induced apoptosis, while treatment of non-stimulated B cells with rolipram or dbcAMP induced a moderate increase in apoptosis, albeit superimposed on considerable basal apoptosis.

BCL-2 and related proteins are likely to regulate sensitivity to apoptosis in CLL and are also potential targets for cAMP-mediated signal-transduction. Although less than 10% of CLL patients have chromosomal translocations involving BCL-2, hypomethylation and high level BCL-2 transcription is common.

I claim:

1. A method, comprising:
    a) providing: i) a patient having of chronic lymphocytic leukemia, and ii) a formulation comprising rolipram; and
    b) administering a therapeutically effective dose of said formulation to said patient under conditions such that said leukemia is reduced.

2. The method of claim 1, wherein said administering is enteral administration.

3. The method of claim 2, wherein said enteral administration is oral administration.

4. The method of claim 1, wherein said administering is parenteral administration.

5. The method of claim 1, wherein said patient is a naive patient.

6. The method of claim 1, wherein said patient is immunocompromised.

7. The method of claim 1, wherein said patient is unresponsive to chemotherapy winth alkylating agents.

* * * * *

UNITED STATES PATENT AND TRADEMARK OFFICE
CERTIFICATE OF CORRECTION

PATENT NO. : 6,399,649 B1
DATED : June 4, 2002
INVENTOR(S) : Adam Lerner

It is certified that error appears in the above-identified patent and that said Letters Patent is hereby corrected as shown below:

<u>Column 15,</u>
Line 17, should read --
1. A method, comprising:
a) providing: i) a patient having chronic lymphocytic leukemia, and ii) a formulation comprising rolipram; and --

<u>Column 16,</u>
Line 1, should read --
(b) administering a therapeutically effective dose of said formulation to said patient under conditions such that said leukemia is reduced. --

Signed and Sealed this

Twenty-third Day of December, 2003

JAMES E. ROGAN
*Director of the United States Patent and Trademark Office*